United States Patent [19]

Pieterse et al.

[11] Patent Number: 5,696,780
[45] Date of Patent: Dec. 9, 1997

[54] FREQUENCY CONVERSION SYSTEM

[75] Inventors: Jan-Willem Pieterse, San Jose; James D. Kafka, Mountain View; Shinan S. Sheng, Saratoga; William L. Nighan, Jr., Menlo Park, all of Calif.

[73] Assignee: Spectra-Physics Lasers, Inc., Mountain View, Calif.

[21] Appl. No.: 680,576

[22] Filed: Jul. 12, 1996

Related U.S. Application Data

[63] Continuation-in-part of Ser. No. 446,203, May 19, 1995, which is a continuation-in-part of Ser. No. 191,656, Feb. 4, 1994, Pat. No. 5,446,749.

[51] Int. Cl.$^6$ .................................................. H01S 3/698
[52] U.S. Cl. .......................... 372/19; 372/22; 372/97; 372/69; 359/328
[58] Field of Search .......................... 372/97, 21, 22, 372/69, 79, 92; 359/328

[56] References Cited

U.S. PATENT DOCUMENTS 5,446,749  8/1995  Nighan, Jr. et al. .............. 372/22

Primary Examiner—Leon Scott, Jr.
Attorney, Agent, or Firm—Wilson Sonsini Goodrich & Rosati

[57] ABSTRACT

A multi-axial mode frequency conversion system includes two resonators. At least two resonator mirrors define a first resonator cavity. A gain medium is positioned in the first resonator cavity. A pump source supplies energy to the gain medium. The first resonator cavity produces a first beam with a plurality of axial modes that are incident on a doubling crystal in the first resonator and produce a frequency doubled output beam. The first resonator cavity provides a sufficient number of axial modes to oscillate so that the doubled output beam has a noise of less than 3% RMS. At least two resonator mirrors define a second resonator cavity coupled to the output beam from the first resonator cavity. The second resonator is configured to provide resonant enhancement of at least a portion of the plurality of axial modes. A non-linear optical material is positioned in the second resonator and configured to produce a harmonic output beam.

25 Claims, 6 Drawing Sheets

FIG.—5

FREQUENCY CONVERSION SYSTEM

CROSS-REFERENCE TO RELATED APPLICATIONS

This application is a continuation-in-part of U.S. patent application Ser. No. 08/446,203, filed May 19, 1995, which is a continuation-in-part of U.S. patent application Ser. No. 08/191,656, filed Feb. 4, 1994 now U.S. Pat. No. 5,446,749, which is incorporated herein by reference.

This application also cross-references U.S. patent application Ser. No. 08/446,195, filed May 19, 1995.

FIELD OF THE INVENTION

This invention relates generally to resonant enhancement of laser radiation and more particularly to resonant enhancement of diode pumped intracavity frequency doubled lasers that are multi-axial mode and exhibit high amplitude stability.

BACKGROUND OF THE INVENTION

Optical resonance has been used to enhance the efficiency of optical second harmonic generation and mixing. For many years external cavities have been used for the resonant enhancement of laser radiation for harmonic generation of single frequency lasers. See Ashkin et al., IEEE Journal of Quantum Electronics, Vol. QE-2, No. 6, June 1966, pp 109–124. Ashkin et al., used a laser source, an external resonator and a KDP sample. The external resonator consisted of a pair of dielectrically coated mirrors which were adjusted in angle and whose separation could be varied by piezoelectrically scanning one of them. By changing mirrors in the external resonator, it was possible to study the resonance of the harmonic and the fundamental separately. Ashkin et al., emphasized that the optimum signal sources for resonant nonlinear effects were in a single transverse and longitudinal mode.

More recently, a system including an enhancement cavity for a mode-locked laser was disclosed by Persaud et al., IEEE Journal of Quantum Electronics, Vol 26, No. 7, July 1990, pp 1253–1258. The system consisted of a synchronously pumped mode-locked coumarin 102 dye laser mode-matched into an enhancement ring cavity with a mode spacing tuned to the repetition rate of the dye laser. Frequency modulation was applied to mode-locked pulses which enabled the dye laser to be locked to a cavity resonance with similar stability to single-frequency locking techniques.

To date resonance enhancement has only been applied to harmonic generation of single frequency lasers or mode locked lasers.

Not all laser systems are single frequency or mode-locked. In fact most lasers run on multiple longitudinal modes where the phase between the modes varies in time (their modes are not locked). For purposes of this disclosure these lasers are referred to as "multi-axial mode" systems. Frequency conversion of multi-axial mode systems is problematic since they typically produce an RMS noise of 10% or greater.

It would be highly desirable to provide a multi-axial mode frequency conversion system that provides resonant enhancement of a plurality of axial modes to produce a high power output beam with a noise of less than 3% RMS.

SUMMARY OF THE INVENTION

It is an object of the invention to provide a multi-axial mode frequency conversion system.

Another object of the invention is to provide a multi-axial mode frequency conversion system with a quiet multi-axial mode first resonator and a second resonator including a non-linear optical material.

A further object of the invention is to provide a multi-axial mode frequency conversion system that provides an output beam with a noise of less than 3% RMS.

These and other objects of the invention are achieved in a multi-axial mode frequency conversion system that includes two resonators. At least two resonator mirrors define a first resonator cavity. A gain medium is positioned in the first resonator cavity. A pump source supplies energy to the gain medium. The first resonator cavity produces a first beam with a plurality of axial modes that are incident on a doubling crystal in the first resonator and produce a frequency doubled output beam. The first resonator cavity provides a sufficient number of axial modes to oscillate so that the doubled output beam has a noise of less than 3% RMS. At least two resonator mirrors define a second resonator cavity coupled to the output beam from the first resonator cavity. The second resonator is configured to provide resonant enhancement of at least a portion of the plurality of axial modes. A non-linear optical material is positioned in the second resonator and configured to produce a harmonic output beam.

The pump source can be a diode pump source including but not limited to a diode bar or a plurality of diode bars. The diode pump source can be fiber-coupled. The non-linear optical material can be a doubling crystal, a frequency mixing crystal or an optical parametric crystal. The optical length of the second resonator is substantially the same as the optical length of the first resonator, an integer multiple of an optical length of the first resonator or an integer submultiple of an optical length of the first resonator.

In one embodiment, the optical length of the second resonator is sufficient to enhance at least 10 axial modes in the second resonator cavity. In another embodiment, the optical length of the second resonator is sufficient to enhance at least 100 axial modes in the second resonator cavity.

A variety of different gain medium are used including but not limited to, Nd:YLF, Nd:YVO$_4$, Nd:YAG, and Nd:LMA. A variety of different non-linear optical materials are used including but not limited to LBO, BBO, KTP, KD*P and KNbO$_4$.

The frequency conversion system produces output beams of varying wavelengths including but not limited to 266 nm, 335 nm and 229 nm. In one embodiment, the output power of the first resonator is 2 W or greater. In one embodiment, the output power of the second resonator is 0.2 W or greater.

DETAILED DESCRIPTION OF THE DRAWINGS

DETAILED DESCRIPTION OF THE PREFERRED EMBODIMENTS

Figure 1:
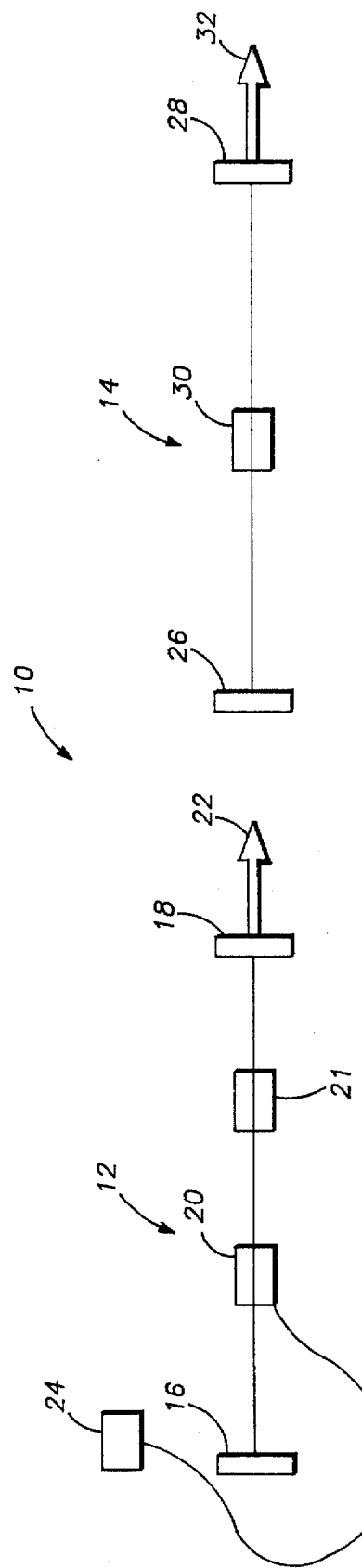
FIG. 1 is a schematic diagram of the frequency conversion system of the present invention.

Referring now to FIG. 1, a multi-axial mode frequency conversion system 10 includes a first resonator 12 and a second resonator 14. A high reflector 16 and an output coupler 18 define first resonator cavity 12. A gain medium 20 is positioned in first resonator cavity 12. A doubling crystal 21 is positioned in first resonator cavity 12 and produces a doubled output beam 22 with a plurality of axial modes. A pump source 24 is coupled to gain medium 20. A high reflector 26 and an output coupler 28 define a second resonator cavity 14 that is coupled to first output beam 22 from first resonator cavity 12. Second resonator 14 is configured to provide resonant enhancement of the plurality of axial modes. A non-linear optical material 30 is positioned in second resonator cavity 14 and configured to produce a harmonic output beam 32 with a noise of less then 3% RMS.

A variety of different materials are used for gain medium 20 including but not limited to Nd:YLF, Nd:YVO$_4$, Nd:YAG, or Nd:LMA. Nd:YVO$_4$ is a preferred material for certain applications.

A variety of different materials are used for doubling crystal 21 including but not limited to BBO, LBO, KTP, KD*P or KNbO$_4$.

Pump source 24 can be a variety of different pump sources including but not limited to a diode pump source such as a diode bar or a plurality of diode bars. When pump source 24 is a diode pump source it can be fiber-coupled.

A non-linear optical material 30 is positioned in second resonator cavity 14. Non-linear optical material can be a variety of different materials including but not limited to a doubling crystal, a frequency mixing crystal or an optical parametric crystal.

A variety of different materials are used for non-linear optical material 30 including but not limited to BBO, LBO, KTP, KD*P or KNbO$_4$.

In order to achieve axial mode enhancement the optical length of second resonator cavity 14 is, (i) substantially the same as the optical length of first resonator cavity 12, (ii) an integral multiple of an optical length of the length of first resonator cavity 12 or (iii) an integral submultiple of an optical length of first resonator cavity 12. Preferably, the optical length of first resonator cavity 12 is sufficient to produce 10 or more axial modes, and in one embodiment, 100 or more axial modes. Correspondingly, the optical length of second resonator cavity 14 is sufficient to enhance 10 or more axial modes, and 100 or more axial modes, respectively. The optical lengths of first and second resonator cavities 12 and 14 may be 1 m or greater.

Depending on the selection of gain medium 20 and the selection of a doubling crystal the wavelength of doubled output beam 22 varies. In one embodiment, Nd:YVO$_4$ can generate a multi-axial mode output at 1340 nm, 1064 nm or 910 nm. Frequency doubled output beam 22 is than produced at 670 nm, 532 nm or 457 nm respectively. When non-linear optical material 30 is a frequency doubling crystal, harmonic output beam 32 is at 335 nm, 266 nm or 229 nm respectively.

A variety of different output powers are achievable. In various embodiments, the output power of first resonator cavity 12 is 2 W or greater, and the output power of second resonator 14 is 0.2 or greater.

Figure 2:
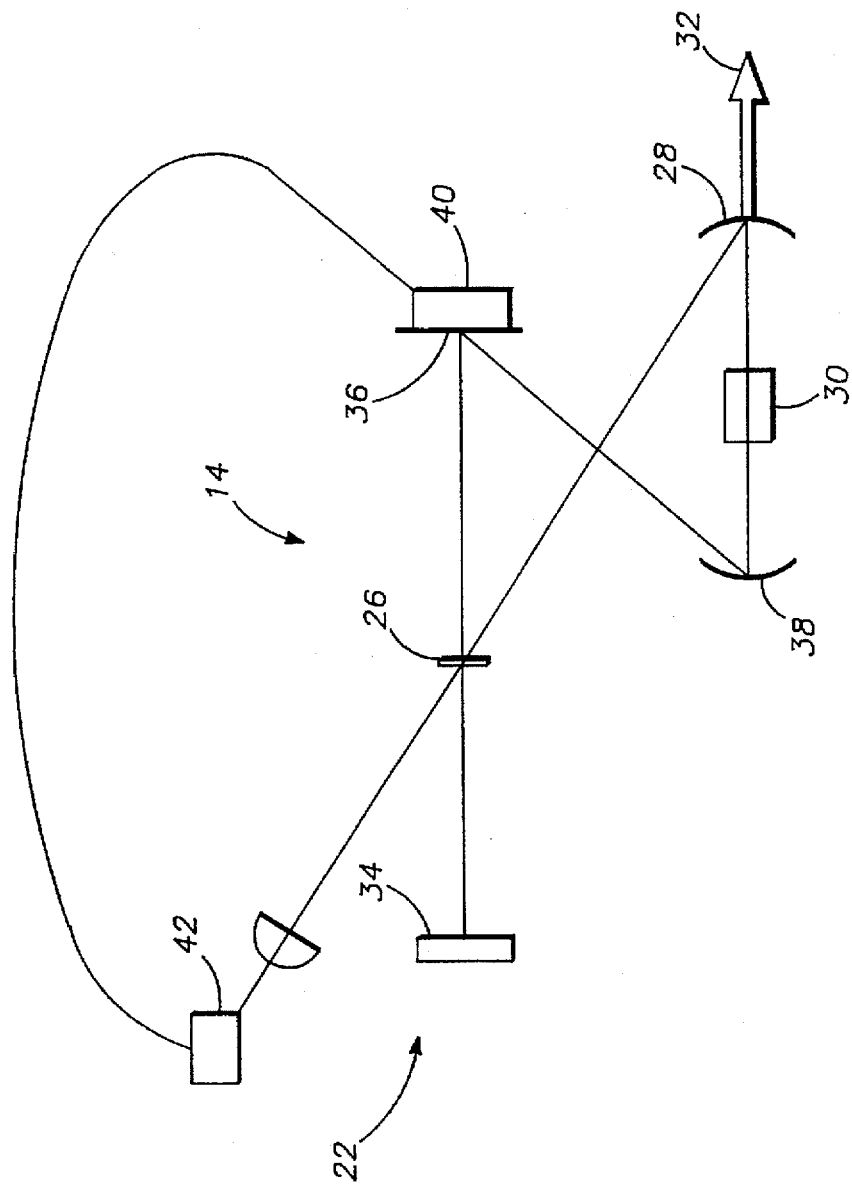
FIG. 2 is a schematic diagram of one embodiment of the second resonator of the frequency conversion system of FIG. 1.

FIG. 2 illustrates an embodiment where second resonator cavity 14 has a ring geometry. A telescope 34 is positioned along the path of doubled output beam 22. Telescope 34 is used to match the spatial modes of first and second resonators 12 and 14. Second resonator cavity 14 is defined by mirrors 26, 36, 38 and 28. In one embodiment, non-linear optical material 30 is BBO cut at Brewsters Angle, and mirrors 36, 38 and 28 are high reflectors at 532 nm. Mirror 26 is an input coupler which is 90–100% reflective at 532 nm. A piezoelectric translator 40 is positioned adjacent to mirror 36 and is used to match the axial modes. A portion of doubled output beam 22 is reflected from mirror 26 and detected at a diagnostic system 42 that is coupled to piezoelectric translator 40. Diagnostic system 42 with piezoelectric translator 40 are commercially available from LAS GMbH, Germany.

Figure 3:
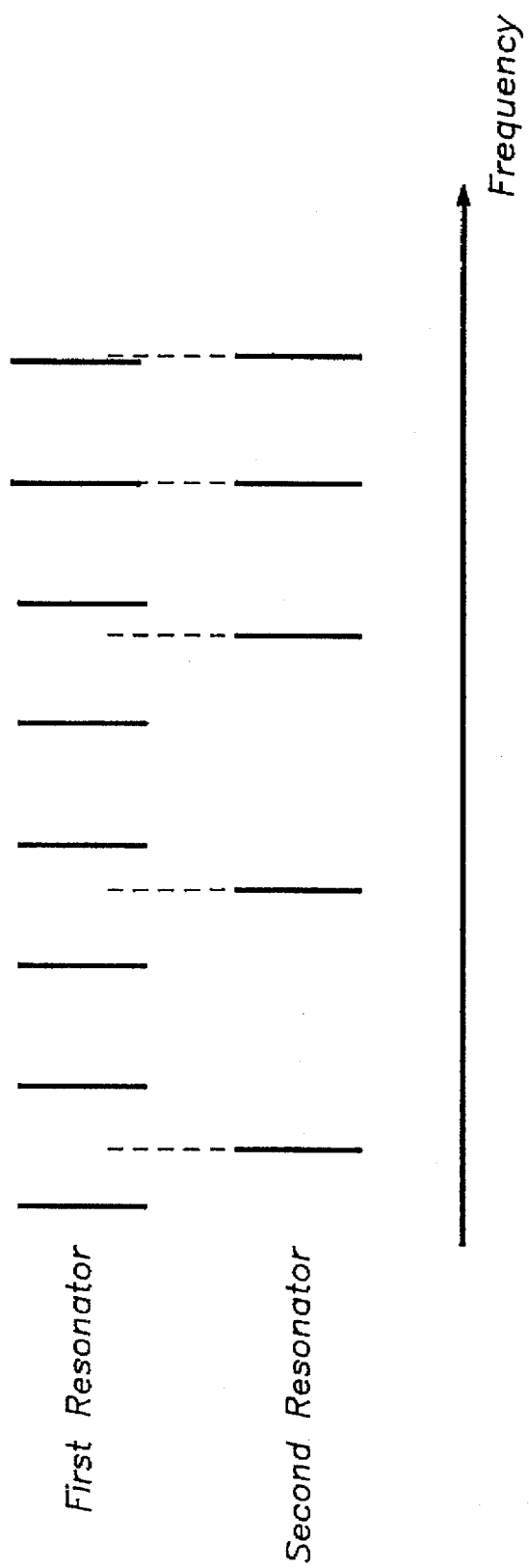
FIG. 3 illustrates the axial modes of the first and second resonators when the optical lengths of the two resonators are not equal.
Figure 4:
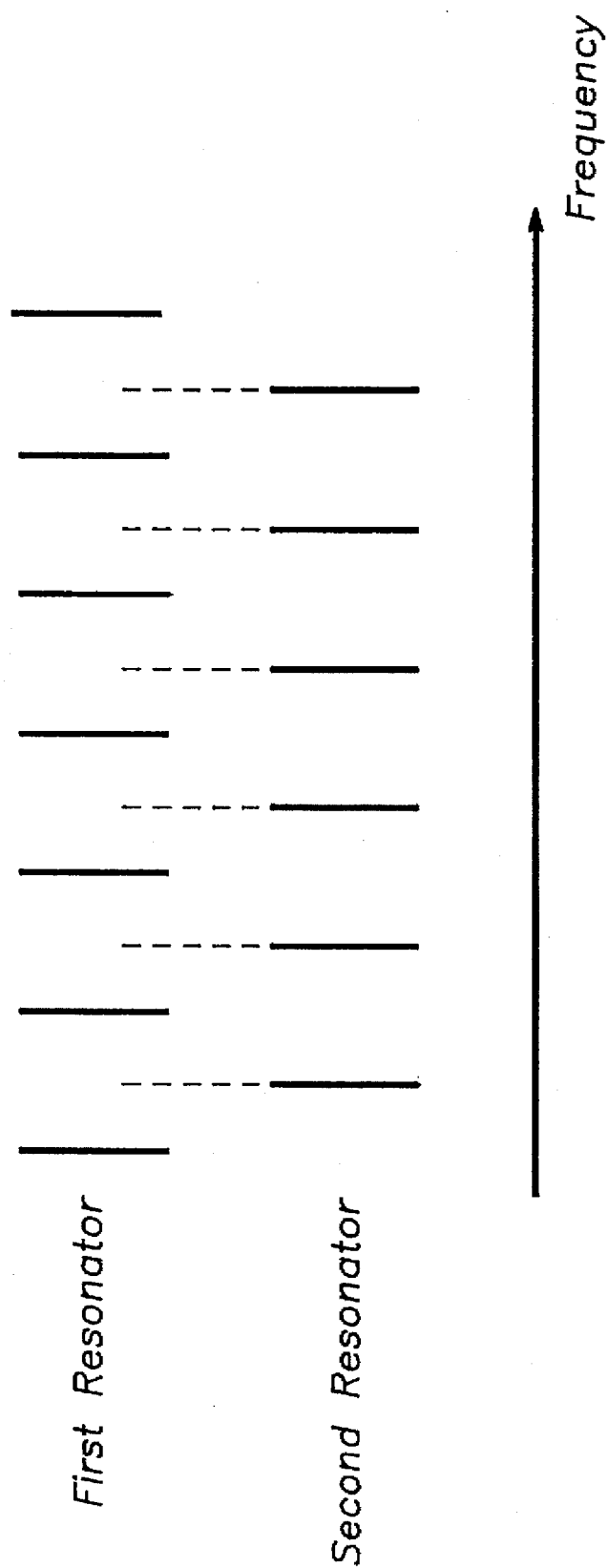
FIG. 4 illustrates the mismatch of the axial modes of the first and second resonators.
Figure 5:
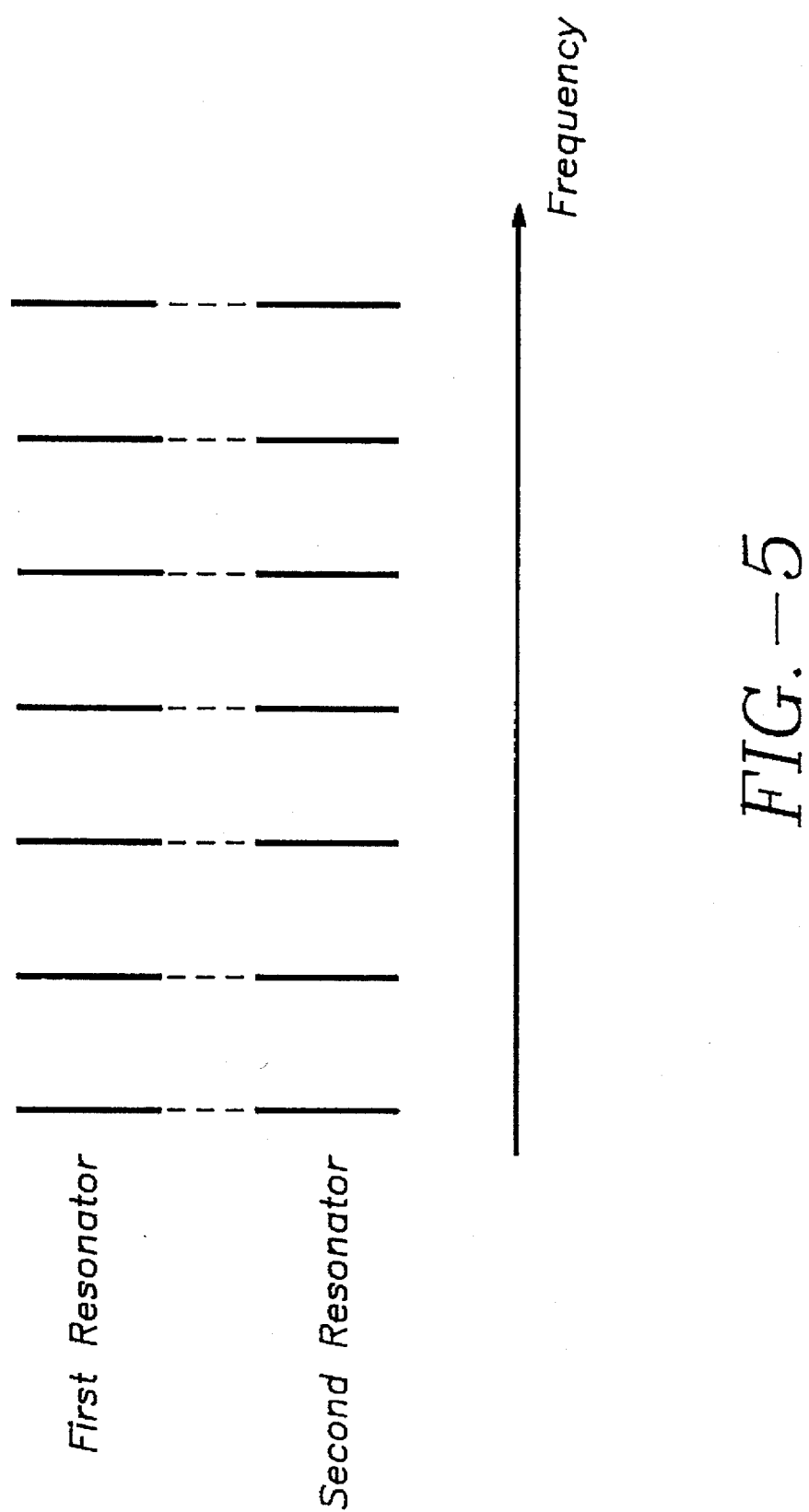
FIG. 5 illustrates the matching of the axial modes of the first and second resonators.

It is necessary that the longitudinal modes of resonators 12 and 14 be nearly identical for enhancement to occur. FIG. 3 illustrates when the optical length of second resonator cavity 14 is too small. In this case the spacing between the modes of second resonator 14 are too large and only a few of the modes from first resonator 12 are enhanced. In FIG. 4, first and second resonator cavities 12 and 14 have nearly the same optical lengths but second resonator 14 is ½ wavelength of light too long. There is a mismatch of the axial modes of resonators 12 and 14 and no enhancement will occur. FIG. 5 illustrates enhancement of all of the axial modes of resonator cavity 12 by resonator cavity 14.

First resonator 12 contains both doubling crystal 21 and gain medium 20 which is pumped. Because of gain medium 20, first resonator 12 is referred to as a hot cavity. Generally the spacing between each of the axial modes in a hot cavity is not exactly the same. Second resonator 14 contains doubling crystal 30 and is nearly a cold cavity. For second resonator 14 the spacing between each of the axial modes will be nearly equal. Thus when matching a cold cavity to a hot cavity, the mode matching illustrated in FIG. 5 is only true for a portion of modes. In one embodiment about 40% of the axial modes can be matched at one time. It is possible to add a gain medium, a saturable absorber, or a dispersive device including a piece of glass of a prism pair to either the hot or the cold cavity in order to make a larger portion of the modes match.

Figure 6:
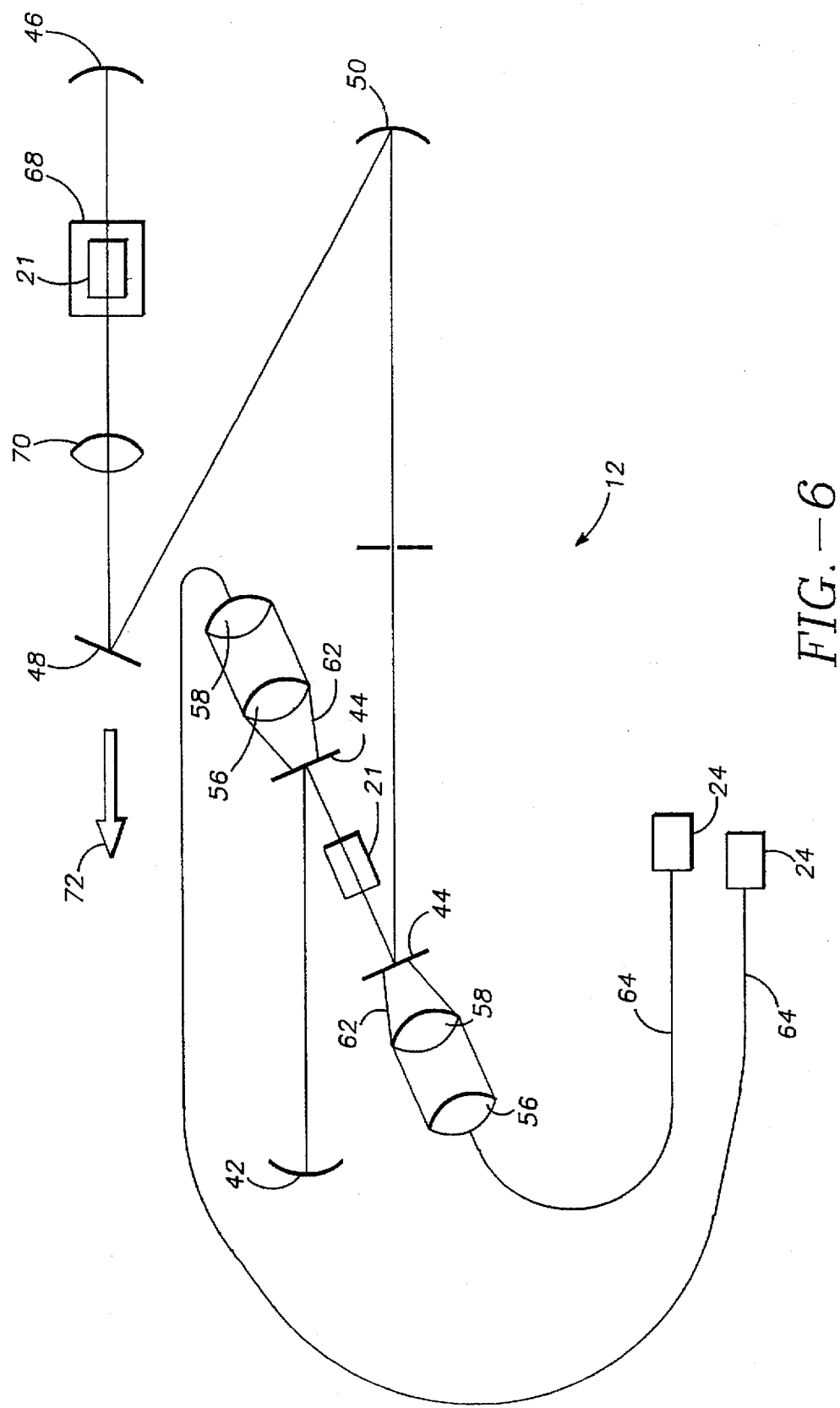
FIG. 6 is a schematic diagram of a diode pumped, multi-axial mode, intracavity doubled first resonator with high amplitude stability.

In FIG. 6, an embodiment of first resonator 12 for 532 nm is illustrated. A suitable first resonator 12 is commercially available from Spectra-Physics Lasers, Mountain View, Calif., called the Millennia. In the illustrated embodiment, first resonator cavity 12 has a total optical length L. First resonator 12 is defined by a high reflector 42, which is highly reflective at 1064 nm, a pair of highly reflective mirrors 44 that are highly reflective at 1064 nm and highly transmissive at 809, a high reflector 50 (preferably curved) highly reflecting at 1064, an output coupler 48 that is highly reflecting at 1064 nm and highly transmissive at 532 nm and end mirror 46 highly reflective at both 1064 nm and 532 nm. Although the optical elements in this embodiment are specific for 1064 nm, 532 nm and 809 nm, it will be appreciated that the optical elements can have other transmission and reflectivity characteristics.

Diode pump source 24 produces a pump beam 62 that is focussed to a desired size by lenses 56 and 58. The size of pump beam 62 is optimized with lenses 56 and 58 to avoid fracture of incident faces of gain mediums 20 while increasing useful pump power.

Diode pump source 24 is coupled to one or more optical fibers 64. Preferably, a bundle of optical fibers 64 is utilized. Coupling of optical fibers 64 to diode pump source 24 can be achieved as taught in U.S. Pat. No. 5,127,068.

A doubling crystal 21 is positioned in first resonator 12. In one embodiment, doubling crystal 21 is LBO. When LBO is used a heating element 68 is included.

In one embodiment, a frequency doubled Nd:YVO$_4$ laser 12 produces 5 W of quiet multi-axial mode output at 532 nm. Second resonator 14 is configured as a ring resonator with a 1% input coupler 26 and a 6 mm long Brewster angled BBO crystal used as doubling crystal 30. When the cavity length is locked with a servo system 42 (Hansch-Couillaud) more than 150 mW is produced at 266 nm.

The output power of harmonic beam 32 can be limited by damage or thermal effects in doubling crystal 30. This can be remedied by using larger spot sizes in doubling crystal 30 since decreasing the average power per unit area (Watts/cm$^2$) reduces these problems. To regain the conversion a high power source for first resonator 12 can be used and/or the length of doubling crystal 30 can be increased.

Although a green output beam has been described, blue, red, near infrared and beams of other wavelengths are possible, depending on the choice of laser and doubling crystals.

Changes and modifications in the specifically described embodiments can be carried out without departing from the scope of the invention which is intended to be limited only by the scope of the appended claims.

What is claimed is:

1. A multi-axial mode frequency conversion system, comprising:

at least two resonator mirrors defining a first resonator cavity;

a gain medium positioned in the resonator cavity;

a pump source supplying energy to the gain medium, wherein the first resonator cavity produces a first beam with a plurality of axial modes incident on a doubling crystal positioned in the first resonator to produce a frequency doubled output beam, the resonator cavity providing a sufficient number of axial modes to oscillate so that the doubled output beam has a noise of less than 3% RMS;

at least two resonator mirrors defining a second resonator cavity coupled to the first beam from the first resonator cavity and configured to provide resonant enhancement of at least a portion of the plurality of axial modes; and a non-linear optical material positioned in the second resonator cavity to produce a harmonic output beam with resonant enhancement of at least a portion of the plurality of axial modes.

2. The frequency conversion system of claim 1, wherein the pump source is a diode pump source.

3. The frequency conversion system of claim 1, wherein the pump source is a diode bar or a plurality of diode bars.

4. The frequency conversion system of claims 1, wherein the pump source is a fiber-coupled diode bar.

5. The frequency conversion system of claim 1, wherein the non-linear optical material is a doubling crystal.

6. The frequency conversion system of claim 1, wherein the non-linear optical material is a frequency mixing crystal.

7. The frequency conversion system of claim 1, wherein the non-linear optical material is an optical parametric crystal.

8. The frequency conversion system of claim 1, wherein an optical length of the second resonator is substantially the same as an optical length of the first resonator.

9. The frequency conversion system of claim 1, wherein an optical length of the second resonator is equal to an integer multiple of an optical length of the first resonator.

10. The frequency conversion system of claim 1, wherein an optical length of the second resonator is equal to an integer submultiple of an optical length of the first resonator.

11. The frequency conversion system of claim 1, wherein the first resonator cavity has a sufficient optical length to produce at least 10 axial modes in the first resonator cavity.

12. The frequency conversion system of claim 11, wherein the second resonator cavity has a sufficient optical length to enhance at least 10 axial modes in the second resonator cavity.

13. The frequency conversion system of claim 1, wherein the first resonator cavity has a sufficient optical length to produce 10 or more axial modes in the first resonator cavity.

14. The frequency conversion system of claim 13, wherein the second resonator cavity has a sufficient optical length to enhance 100 or more axial modes in the second resonator cavity.

15. The frequency conversion system of claim 1, wherein the first resonator cavity has an optical length of 1 m or greater.

16. The frequency conversion system of claim 15, wherein the second resonator cavity has an optical length of 1 m or greater.

17. The frequency conversion system of claim 1, wherein the gain medium is selected from the group consisting of Nd:YLF, Nd:YVO$_4$, Nd:YAG, and Nd:LMA.

18. The frequency conversion system of claim 1, wherein the gain medium is Nd:YVO$_4$.

19. The frequency conversion system of claim 1, wherein the non-linear optical material in the second resonator is selected from the group consisting of LBO, BBO, KTP, KD*P and KNbO$_4$.

20. The frequency conversion system of claim 1, wherein the non-linear optical material in the second resonator is BBO.

21. The frequency conversion system of claim 1, wherein the second resonator output beam has a wavelength of about 266 nm.

22. The frequency conversion system of claim 1, wherein the second resonator output beam has a wavelength of about 335 nm.

23. The frequency conversion system of claim 1, wherein the second resonator output beam has a wavelength of about 229 nm.

24. The frequency conversion system of claim 1, wherein an output power of the first resonator is 2 W or greater.

25. The frequency conversion system of claim 1, wherein an output power of the second resonator is 0.2 W or greater.

* * * * *